(12) United States Patent
Amit et al.

(10) Patent No.: US 8,940,888 B2
(45) Date of Patent: Jan. 27, 2015

(54) HYDRAZIDO DERIVATIVES OF HYALURONIC ACID

(71) Applicant: Prochon Biotech Ltd., Ness Ziona (IL)

(72) Inventors: Boaz Amit, Kiron (IL); Avraham Wortzel, Rishon le Zion (IL); Avner Yayon, Moshav Sitria (IL)

(73) Assignee: Prochon Biotech Ltd., Waltham, MA (US)

( * ) Notice: Subject to any disclaimer, the term of this patent is extended or adjusted under 35 U.S.C. 154(b) by 0 days.

(21) Appl. No.: 14/013,454

(22) Filed: Aug. 29, 2013

(65) Prior Publication Data

US 2014/0005141 A1 Jan. 2, 2014

Related U.S. Application Data

(63) Continuation of application No. 12/282,129, filed as application No. PCT/IL2007/000284 on Mar. 6, 2007, now Pat. No. 8,524,885.

(60) Provisional application No. 60/779,423, filed on Mar. 7, 2006.

(51) Int. Cl.

| *C08B 37/08* | (2006.01) |
| *A61K 31/728* | (2006.01) |
| *A61K 47/36* | (2006.01) |
| *A61K 8/73* | (2006.01) |
| *A61K 38/18* | (2006.01) |
| *A61K 31/726* | (2006.01) |
| *A61K 47/48* | (2006.01) |
| *A61K 49/00* | (2006.01) |
| *A61Q 19/00* | (2006.01) |

(52) U.S. Cl.
CPC ......... *C08B 37/0072* (2013.01); *A61K 38/1825* (2013.01); *A61K 31/728* (2013.01); *A61K 8/735* (2013.01); *A61K 31/726* (2013.01); *A61K 47/4823* (2013.01); *A61K 49/0043* (2013.01); *A61K 49/0054* (2013.01); *A61Q 19/00* (2013.01)
USPC ............. 536/55.2; 536/53; 536/54; 536/55.1; 536/55.3; 514/54; 514/56; 424/422; 424/488

(58) Field of Classification Search
None
See application file for complete search history.

(56) References Cited

U.S. PATENT DOCUMENTS

| 4,582,865 A | 4/1986 | Balazs et al. |
| 4,713,448 A | 12/1987 | Balazs et al. |
| 5,356,883 A | 10/1994 | Kuo et al. |
| 5,616,568 A | 4/1997 | Pouyani et al. |
| 5,874,417 A | 2/1999 | Prestwich et al. |
| 6,630,457 B1 | 10/2003 | Aeschlimann et al. |
| 7,767,806 B2 | 8/2010 | Hirakura et al. |

FOREIGN PATENT DOCUMENTS

| WO | WO0241877 A1 | 5/2002 |
| WO | WO2004060404 A1 | 7/2004 |
| WO | WO2005023906 A1 | 3/2005 |
| WO | WO2006001046 A1 | 1/2006 |

OTHER PUBLICATIONS

Shaklee, P. et al "Hydrazinolysis of heparin and other glycosaminoglycans"; Biochem. J. (1984) vo1217, pp. 187-197.
Paul Bulpitt et al., New Strategy for Chemical Modification of Hyaluronic Acid: Preparation of Funtionalized Derivatives and Their Use in the Formation of Novel Biocompatible Hydrogels, Journal of Biomedical Materials Research, (1999), pp. 152-169.
Kelly R. Kirker et al., Gl Ycosaminogl Ycan Hydrogel Films as Bio-Interactive Dressing for Wound Healing, Biomaterials, vol. 23, (2002), pp. 3661-3671.
Hao Li et al., Synthesis and Biological Evaluation of a Cross-Linked Hyaluronan-Mitomycin C Hydrogel, Biomacromolecules, (2004), pp. 895-902, vol. 5.
Yi Luo et al., Synthesis and Selective Cytotoxicity of a Hyaluronic Acid-Antitumore Bioconjugate, Bioconjugate Chemicals, (1999), pp. 755-763, vol. 10.
Tara Pouyani et al., Functionalized Derivatives of Hyaluronic Acid Oligosaccharides: Drug Carriers and Novel Biomaterials, Bioconjugate Chemicals, (1994), vol. 5, pp. 339-347.
Glenn D. Prestwich et al., Controlled Chemical Modication of Hyaluronic Acid: Synthesis, Application, and Biodegradation of Hydrazide Derivatives, Journal of Controlled Release, vol. 53, (1998), pp. 93-103.
Xiao Zheng Shu et al., Attachment and Spreading of Fibroblasts on an RGD Peptide-Modified Injectable Hyaluronan Hydrogel, Wiley periodicals, (2003).

*Primary Examiner* — Leigh Maier
(74) *Attorney, Agent, or Firm* — Brown Rudnick LLP; Thomas C. Meyers

(57) ABSTRACT

Disclosed are chemically modified hyaluronic acid (HA) derivatives containing hydrazido groups directly linked to the glucuronic acid residues of HA. Said hydrazido groups are used to obtain crosslinked and labeled HA derivatives. The invention further relates to methods of preparation of said HA derivatives.

14 Claims, No Drawings

HYDRAZIDO DERIVATIVES OF HYALURONIC ACID

FIELD OF THE INVENTION

The present invention relates to chemically modified hyaluronic acid derivatives containing directly linked hydrazido groups and to labeled and cross-linked derivatives thereof. The invention further relates to methods for the preparation of said HA derivatives.

BACKGROUND OF THE INVENTION

Glycosaminoglycans (GAGs) which are part of the extra cellular matrix (ECM) can be chemically modified and adapted for medical use.

Hyaluronic acid (HA), which is the only known unsulfated GAG, is a ubiquitous component of the ECM of all connective tissues. It is a linear polysaccharide composed of a disaccharide repealing unit. The components of the disaccharide unit are N-acetyl-D-glucosamine and D-glucuronic acid linked by β1-4 and β1-3 linkages. HA has a range of naturally occurring molecular masses from several thousands to over 10 million Daltons.

Due to its unique physiochemical properties, HA has been implicated in water homeostasis of tissues, in regulating the permeability of other substances and in lubricating joints. HA binds specifically to proteins in the ECM and on the cell surface. These interactions are important in stabilizing the cartilage matrix, in cell motility, in cellular proliferation, in wound healing, in inflammation as well as in cancer metastasis (Morra, Biomacromolecules 6:1205-1223, 2005; Vercruysse and Prestwich, Critical Reviews in Therapeutic Drug Carrier Systems 15(5):513-555, 1998; Entwistle et al., J. Cell Biochem. 61:569-577, 1996). The unique viscoclastic nature of HA along with its biocompatibility and non-immunogenicity has led to its use in a number of clinical applications, which include: treatment of osteoarthritis of the knee, surgical aid in eye surgery, and healing and regeneration of surgical wounds (Goldberg and Buckwalter, Osteoarthritis Cartilage 13(3):216-224, 2005; Brown and Jones, J. Eur. Acad. Dermatol. Venereol. 19(3):308-318, 2005).

A variety of chemical modifications of native HA have been proposed to improve its mechanical and chemical properties. The principal targets for chemical modifications of HA are the hydroxyl and carboxyl functions.

Modifications via the hydroxyl function are mainly used for preparation of cross-linked HA by reaction with bifunctional cross-linkers e.g. divinyl sulfone and diglycidyl ethers (U.S. Pat. Nos. 4,582,865 and 4,713,448).

Modifications of the carboxylic functions are mainly used to introduce pendant functionalities that further permit attachment of drugs and biochemical reagents (Li et al., Biomacromolecules 5:895-902, 2004; Shu et al., J. Biomed. Mater. Res. 68A:365-375, 2004). Modifications of the carboxylic groups can also be used to obtain cross-linked products (Bulpitt and Aeschlimann, J. Biomed. Mater. Res. 47:152-169, 1999).

These modifications are made using hydrazides or amines. The activation of the carboxylic functions of HA towards nucleophilic attack by hydrazides or amines, in aqueous media, is mainly performed by the use of water soluble carbodiimides, especially 1-ethyl-3-[3-dimethylaminopropyl] carbodiimide (EDC). Two major procedures for performing this activation are known in the art. The first one was developed by Prestwich et al. and is disclosed in U.S. Pat. No. 5,616,568, U.S. Pat. No. 5,874,417, (Prestwich et al., J. Controlled Release 53:93-103, 1998, and Pouyani and Prestwich, Bioconjugate Chem. 5:339-347, 1994). According to this procedure, HA is reacted with EDC under mildly acidic conditions (e.g. pH 4.75), to produce an active unstable O-acylisourea intermediate. Hydrazides that have a low pKa of 3-4 and retain their nucleophilicity at pH 4.75 efficiently react with the O-acylisourea intermediate to produce hydrazido derivatives of the glucuronic acid residues. In contrast, primary amines which are not nucleophiles at this pH failed to react with the active intermediate which eventually rearranges to a stable N-acylurea derivative.

The use of dihydrazide compounds such as adipic dihydrazide (ADH) provided derivatives of the formula HA-CO—NH—NH—CO—$(CH_2)_4$—CO—NH—$NH_2$ (HA-ADH) having multiple pendant hydrazido groups for further derivatization with drugs, biochemical probes and cross-linking reagents.

Later publications demonstrated conjugation of the antitumor drug Taxol to the HA-ADH derivative (Luo and Prestwich, Bioconjugate Chem. 10:755-763, 1999) and the preparation of hydrogel films as bio-interactive dressings for wound healing from the HA-ADH derivative cross-linked with poly(ethyleneglycol)propiondialdehyde (Kirker et al., Biomaterials 23:3661-3671, 2002).

A second procedure for the activation of the carboxylic functions of HA was developed by Bulpitt and Aeschlimann (J. Biomed. Mater. Res. 47:152-169, 1999) and U.S. Pat. No. 6,630,457. According to this procedure, HA is reacted at pH 6.8 with a combination of EDC and the additive 1-hydroxybenzotriazole (HOBt). Initially, the carbodiimide and the carboxylate anion react to produce an active unstable O-acylisourea intermediate, which further reacts with the additive to form a more hydrolysis-resistant and non-rearrangeable active ester. This active ester readily reacts with hydrazides as well as with certain animes (which are present in an unprotonated form at pH of about 5.5-7.0). The use of this procedure allows the formation of HA derivatives with pendant hydrazido, amino as well as other functional groups.

The abovementioned methods for the introduction of pendant hydrazido groups with adipic dihydrazide (ADH) introduce a non-natural linker entity into the hyaluronic acid. The use of such derivatives for clinical applications inherently introduces these non-natural linker entities into the (human) organism which can lead to unexpected complications. It is therefore highly desirable to avoid the use of such linker moieties. The current invention presents a way to introduce hydrazido groups into HA while avoiding the use of linkers altogether, thereby circumventing possible complications indicated above.

SUMMARY OF THE INVENTION

It has now been found, in accordance with the present invention, that hydrazine itself or a substituted hydrazine can react with hyaluronic acid in the presence of a carbodiimide, thus resulting in compounds in which carboxyl groups of the HA molecule are directly modified to hydrazido groups.

The present invention thus relates, in one aspect, to a hyaluronic acid derivative or a salt thereof, said derivative having a part of the carboxy groups of the D-glucuromic residues converted into hydrazido groups.

The present invention further relates to a method for converting carboxylic groups of HA into hydrazido functions using hydrazine or substituted hydrazine according to the general reaction described in scheme 1.

Scheme 1:

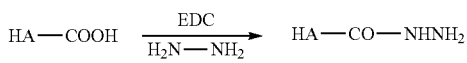

Thus, the HA hydrazido derivatives of the present invention differ from the HA hydrazides previously described in the art by having the hydrazido groups CO—NHNH$_2$ directly linked at the glucuronic acid residues of the hyaluronic acid backbone and not via a spacer.

According to the present invention the generation of a hydrazido modified water-soluble or water-insoluble, cross-linked HA can be determined by the pH of the reaction. In addition, the pH of the reaction determines the amount of hydraxido groups in the hydrazido-modified water soluble HA molecule.

When the reaction is performed under acidic conditions (pH 3.0-5.5) a jelly-like, water insoluble cross-linked product is obtained having an estimated amount of 5-10% hydrazido groups.

When the reaction is performed under slightly acidic or slightly basic conditions (pH 6.0-7.5), a soluble HA molecule is obtained having up to 3% hydrazido groups.

In a preferred embodiment of the invention the reaction is performed in a pH range of about 5.6 to about 5.9 resulting in a water-soluble hydrazido functionalized HA. In a most preferred embodiment, the reaction is performed at pH 5.7-5.9, wherein the reaction results in a water-soluble HA molecule having 11-20% hydrazido groups.

The chemically modified water-soluble and uncross-linked HA-CO—NH—NH$_2$ derivative of the invention may be coupled, through the amine moiety of the hydrazido groups, to additional components such as biocompatible materials, detectable labels, and biologically active materials, e.g., pharmaceutical drugs and bioactive agents.

In one embodiment, the amine moiety of the hydrazido groups is covalently bound to a detectable label containing an amine-specific or amine-reactive group. Detectable labels suitable for this purpose include for example: a fluorescent label, a phosphorescent label, a radiolabel, an affinity label, an electron-spin resonance (ESR) label, detectable nanoparticles such as for example gold and semiconductor nanoparticles, oligonucleotides, polynucleotides, antibodies, enzymes, polymer beads.

The chemically modified soluble HA-CO—NH—NH$_2$ derivative containing the hydrazido groups may also be cross-linked to form hydrogels by using any of the large variety of amine-specific or amine-reactive homobifunctional and heterobifunctional cross-linkers known in the art such as, but not limited to, bisaldehydes (e.g. glutaraldehyde and poly (ethylene glycol) propiondialdehyde), bis-active esters (e.g. disuccinimidyl glutarate and disuccinimidyl suberate), bisimidates (Dimethyl suberimidate), bisacrylates (e.g. poly (ethylene glycol) diacrylate) and bismaleimides (e.g. Bis-maleimidohexane).

The chemically modified soluble HA-CO—NH—NH$_2$ derivative containing the hydrazido groups may also be cross-linked to form hydrogels by using a natural, denaturated or non-natural (synthetic) polyfunctional amine-specific or amine-reactive cross-linking agent (for example a polyaldehyde).

The chemically modified soluble HA-CO—NH—NH$_2$ derivative containing the hydrazido groups may also be cross-linked to form hydrogels using a carbodiimide (such as, but not limited to EDC), thus resulting in a cross-linked compound represented by the formula HA-CO—NH—NH—CO-HA. The cross-linked hydrogel being formed by reaction of a part of the hydrazido groups of the D-glucuronic residues with a part of the carboxy groups of the D-glucuronic residues, said carboxy groups being activated by the carbodiimide.

The cross-linked hydrazido functionalized hyaluronic acid may contain additional components that may be introduced either before or after the crosslinking. These components may include (but are not limited to) pharmaceutical drugs, cosmetic agents, detectable labels, native or synthetic polymers, proteins, polypeptides, oligonucleotides or cells.

Thus, it is to be understood that compositions comprising a pharmaceutical drug or bioactive agent may be either conjugated chemically to the hydrazido functionalized HA or unconjugated. The HA compositions of the present invention that comprise pharmaceuticals or other bioactive moieties are particularly useful as depots for sustained release, controlled release or slow release of the active agents.

The cross-linked hydrazido functionalized hyaluronic acid may serve as an integral scaffolding material for tissue engineering as well as for wound or fracture healing either by itself, or as a substrate for cell delivery, e.g. the delivery of chondrocytes for repairing cartilage damage.

DETAILED DESCRIPTION OF THE INVENTION

The prior art describes HA derivatives containing pendant hydrazido groups attached to the carboxylic functions through a linker. However, there is no disclosure of hydrazido functionalized HA at which the carboxylic groups are directly converted into hydrazido functions.

Two prevailing methods are known for the introduction of pendant hydrazido groups at the glucuronic acid sites of HA. The first method of Prestwich et al. (Bioconjugate Chem. 5:339-347, 1994) comprises reaction of HA with EDC at pH 4.75 to produce an active unstable O-acylisourea intermediate that subsequently reacts with hydrazides having a pKs's of 3-4 that retain their nucleophilicity at pH 4.75.

Bulpitt et al. (J. Biomed. Mater. Res. 47:152-169, 1999) activated the carboxy functions of HA with EDC in the presence of 1-Hydroxybenzotriazole (1-HOBt) at pH 6.8 or sulfo-N-hydroxysuccinimide (sulfo-NHS) at pH 7.5, followed by reaction with certain hydrazides and amines that are still nucleophilic (not protonated) under these conditions.

Attempts to use the abovementioned methods to react the carboxy functions of HA with hydrazine were unsuccessful, the method of Prestwich et al led to a water-insoluble crosslinked hydrazido functionalized product. The procedure of Bulpitt gave water soluble hydrazido derivatives but the amount of hydrazido functions did not exceed 3%.

It was now surprisingly found that the reaction of HA with hydrazine and a carbodiimide at pH 5.7-5.9 leads to water soluble hydrazido derivatives having up to 20% hydrazido functions. This represents a dramatic increase in the amount of the hydrazido functions as compared to those obtained at a pH range of 6.0-7.5.

As described above when the derivatization of HA with hydrazine is carried out under acidic conditions (pH 3.5-5.5), the hydrazido-functionalized HA is always obtained as a water insoluble product. However it was found that water soluble hydrazido-functionalized HA could be obtained under the same acidic conditions provided that part of the carboxylic functions are modified prior to the derivatization reaction with hydrazine. Such modification was obtained by reacting HA with EDC, resulting in the conversion of part of the HA carboxy groups into N-acylurea groups.

The present invention therefore relates to hyaluronic acid derivatives having part of the carboxy groups of the D-glucuronic residues converted into hydrazido groups directly bound to the hyaluronic acid, and to salts thereof.

In one embodiment, the hyaluronic acid derivative is an uncross-linked compound represented by the formula:

HA-CO—NR1-NHR2 wherein R1 and R2, the same or different, each is H, $C_1$-$C_{20}$ alkyl, $C_2$-$C_{20}$ alkenyl, $C_2$-$C_{10}$ alkynyl, $C_6$-$C_{14}$ aryl, alkaryl, arakyl or heterocyclyl optionally substituted by one or more radicals selected from the group consisting of halogen, hydroxy, alkoxy, thioalkyl, nitro, cyano, $CF_3$, $CONH_2$, and —NH—$NH_2$, and/or each of the $C_1$-$C_{20}$ alkyl, $C_2$-$C_{20}$ alkenyl, $C_2C_{10}$ alkynyl may be interrupted by O or S or by a group $N^{30}$ R3R4, wherein R3 and R4, the same or different; each is H, $C_1$-$C_{20}$ alkyl, $C_2$-$C_{20}$ alkenyl, $C_6$-$C_{14}$ aryl.

In one preferred embodiment, R1 and R2 are both hydrogen and the hyaluronic acid derivative is an uncross-linked, water-soluble compound represented by the formula HA-CO—NH—$NH_2$.

In another embodiment, R1 and R2 are both hydrogen and the hyaluronic acid derivative is an uncross-linked, water-soluble compound further containing N-acylurea residues.

In one embodiment, the unsubstituted hydrazines that can be used in the present invention are monosubstituted and disubstituted hydrazines of the formulas HNR1-$NH_2$ and HNR1-NHR2, respectively, wherein R1 and R2, the same or different, is each alkyl optionally substituted by halogen or hydroxy, cycloalkyl, aryl, aralkyl or heterocyclyl. Examples of monosubstituted hydrazines include methyl hydrazine, 2-fluoroethyl hydrazine, cyclopropyl hydrazine, 1-methyl-propyl hydrazine, 2-hydrazino-2-propanol, phenyl hydrazine, 2-nitro-phenyl hydrazine, 4-nitro-phenyl hydrazine, 2,4-dinitro-phenyl hydrazine, p-tolyl hydrazine, benzyl hydrazine, m-hydroxybenzyl hydrazine, napthyl hydrazine, and 5-hydrazino-1,2-oxazol. Examples of 1,2-disubstituted hydrazines include 1,2-dimethyl hydrazine, 1,2-diethyl hydrazine, 1-methyl-2-hydroxyethyl-hydrazine, and 2-(2-methylhydrazino)-ethanol.

In another embodiment, the substituted hydrazines that can be used in the present invention are dihydrazines such as, but not limited to, methylenedihydrazine, ethylenedihydrazine, propylenedihydrazine butylene-dihydrazine, phenylene-dihydrazine, 6,7-dihydrazino-quinoxaline, 1-piperidino-ethyl-enedihydrazine, 1-morpholino-ethylenedihydrazine, 1,1'-(1,2-ethanediyl)bis [hydrazine], 6,7-dihydrazino-quinoxaline, or trishydrazines such as 1,1',1",-(1,2,4-bezenetriyl)tris hydrazine.

The resulting hyaluronic acid derivative may contain between 2% and 70% hydrazido groups, preferably not less than 10%.

In another embodiment, the amine moiety of the hydrazido groups of the uncross-linked, water-soluble compound represented by HA-CO—NH—$NH_2$, is coupled covalently to a detectable label containing an amine-specific or amine-reactive moiety. Said label is selected from the the following (non-limiting) list:

Fluorescent labels, wherein the fluorescent moieties include, but are not limited to: fluorescein, carboxyfluorescein, fluorescein dichlorotriazine (5-DTAF), naphthofluorescein, rhodamine, rhodamine Green, tetramethyl rhodamine, Texas Red, perylene, pyrene, anthracene, naphthalene (e.g. dansyl), stilbene, (bis)-benzoxazole, coumarine derivatives (e.g. Alexa Fluor® derivatives), BODIPY®-derivatives, pyridyloxazoles, dixogenin, phenoxazine, triarylmethanes, xanthen, flavin, porphyrin, cyanin, naphthocyanin, lanthanide-complexes, transition metal complexes, UV-light excitable microspheres, green fluorescent protein.

Phosphorescent labels wherein the phosphorescent moieties include, but are not limited to; Eosine, Erythrosins, luciferin, lumazine, lanthanide complexes, transition metal complexes.

Radiolabels comprising molecules or complexes wherein the radionuclide moiety includes but is not limited to: $^{10}$B, $^{123}$I, $^{124}$I, $^{125}$I, $^{131}$I, $^{76}$Br, $^{77}$Br, $^{35}$Cl, $^{18}$F, $^{3}$H, $^{11}$C, $^{14}$C, $^{13}$N, $^{18}$O, $^{15}$O, $^{32}$P, $^{35}$S, $^{46}$Sc, $^{51}$Cr, $^{52}$Fe, $^{52m}$Mn, $^{57}$Co, $^{61}$Cu, $^{64}$Cu, $^{67}$Cu, $^{67}$Ga, $^{68}$Ga, $^{72}$As, $^{85}$Sr, $^{86}$Y, $^{90}$Y, $^{95}$Nb, $^{97}$Ru, $^{99m}$Tc, $^{103}$Ru, $^{105}$Rh, $^{109}$Cd, $^{61}$Cu, $^{64}$Cu, $^{67}$Cu, $^{67}$Ga, $^{114}$In, $^{133}$Xe, $^{140}$La, $^{141}$Ce, $^{153}$Gd, $^{153}$Sm, $^{157}$Gd, $^{161}$Tb, $^{166}$Ho, $^{169}$Er, $^{169}$Yb, $^{175}$Yb, $^{177}$Lu, $^{186}$Re, $^{188}$Re, $^{203}$Pb, $^{212}$Bi, $^{225}$Ac.

Affinity labels such as biotin and antibodies.

Electron Spin Resonance (ESR) labels: stable nitroxyl radicals such as 2,2,6,6-tetramethyl-4-piperadone-1-oxyl (TEMPO) derivatives, DOXYL-derivatives.

Metal and semiconductor nanoparticles such as gold-nanoparticles, silver nanoparticles, quantum dots, indium-tin-oxide (ITO) nanoparticles, Cadmium selenide (CdSe) nanoparticles, Tungsten sulfide (WS) nanoparticles, Gallium arsenide (GaAs) nanoparticles, Zinc sulfide (ZnS) nanoparticles.

Spectral Colorimetric labels, Proteins, Enzymes such as Horseradish peroxidase and alkaline phosphatase, oligonucleotides and polynucleotides, polymer beads.

In a more preferred embodiment, the amine moiety of the hydrazido groups is coupled covalently to a fluorescent label containing an amine-specific or amine-reactive group, wherein the fluorescent moieties of said label include, hut are not limited to: fluorescein, cafboxyfluorescein, fluorescein dichlorotriazine (5-DTAF), naphthofluorescein, rhodamine, rhodamine Green, tetramethyl rhodamine, Texas Red, perylene, pyrene, anthracene, naphthalene (e.g. dansyl), stilbene, (bis)-benzoxazole, coumarine derivatives (e.g. Alexa Fluor® derivatives), BODIPY®-derivatives, pyridyloxazoles, dixogenin, phenoxazine, triarylmethanes, xanthen, flavin, porphyrin, cyanin, naphthocyanin, lanthanide-complexes, transition metal complexes, UV-light excitable microspheres, green fluorescent protein.

In an even more preferred embodiment, the amine moiety of the hydrazido groups is coupled covalently to the amine-reactive fluorescent label fluorescein isothiocyanate (FITC). The resulting labeled compound can be represented by the formula HA-CO—NH—NH—CS—NH-Fluorescein.

The chemically modified soluble HA-CO—NH—$NH_2$ derivative containing the hydrazido groups may also be cross-linked to form hydrogels.

In one embodiment, the hyaluronic acid derivative is a cross-linked water-insoluble compound formed by reaction of a part of the hydrazido groups of the D-glucoronic residues with a part of the carboxy groups of the D-glucuronic residues, said carboxy groups being activated by a carbodiimide, thus resulting in a cross-linked compound represented by the formula HA-CO—NH—NH—CO-HA.

In another embodiment, the hyaluronic acid derivative is a cross-linked compound in which part of the carboxy groups of the D-glucuronic residues are linked with another part of the carboxy groups of the D-glucuronic residues via hydrazine, said carboxy groups being activated by a carbodiimide resulting in a cross-linked compound represented by the formula HA-CO—NH—NH—CO-HA.

In yet another embodiment, the hyaluronic acid derivative is a cross-linked compound formed by reaction of a part of the hydrazido groups of the D-glucuronic residues with another part of the hydrazido groups of the D-glucuronic residues via an amine-specific or amine-reactive homobifunctional or heterobifunctional linker Y, said cross-linked hyaluronic acid derivative being represented by the formula:

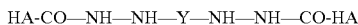

wherein Y is an anliphatic, aromatic, arylaliphatic, cycloaliphatic or heterocyclic chain.

Homobifunctional cross-linkers have two identical reactive groups. Heterobifunctional cross-linkers are defined as having two different reactive groups that allow for sequential conjugation reaction. Examples of amine-specific homobifunctional cross-linkers that can be used in the present invention include, without being limited to, bis(sulfosuccinimidyl) suberate, bis[2-(succinimidooxy-carbonyloxy)ethyl]sulfone, disuccinimidyl suberate, disuccinimidyl tartarate, dimethyl adipimate.2 HCl, dimethyl pimelimidate.2 HCl, dimethyl suberimidate.2 HCl, glutaraldehyde, poly (ethylene glycol-bis-[succinimidyl-[succinate]]. Example of amine-reactive homobifunctional cross-linkers that can also be used in the present invention are bismaleimides (e.g. Bis-maleimidohexane). A non-limiting example of an anime reactive heterobifunctional cross-linker that can also be used in the present invention is succinimidyl 4-(N-maleimidomethyl) cyclohexane-carboxylate.

Polyfunctional crosslinkers contain more than two reactive groups for the formation of cross linkers.

In a further embodiment the hyaluronic acid derivative is a cross-linked compound formed by reaction of a part of the hydrazido groups with another part of the hydrazido groupd via polyfunctional compounds e.g. polyaldehydes.

In a more preferred embodiment, said polyaldehyde is selected from an oxidized collagen, oxidized gelatin and oxidized hyaluronic acid.

In a most preferred embodiment, said polyaldehide is oxidized gelatin.

The cross-linked hyaluronic acid derivative of the invention may further comprise directly linked free hydrazido groups available for further derivatization. These free hydrazido groups can be used for further conjugation of desired pharmacologically or biologically active agents as well as detectable labels as specified above. Alternatively, part of the free hydrazido groups of the water-soluble hyaluronic acid derivative of the invention can be derivatized with a pharmacologically or biologically active agent as well as a detectable; label and then cross-linked into a hydrogel.

A hydrogel should be regarded as a viscous or semi-solid jelly-like macromolecular network structure that swells in water. The macromolecular network is made up of hydrophilic polymer units that are held together either solely by non-covalent bonds or additionally by a certain amount of covalent bonds. The non-covalent hydrogels, better known as uncross-linked networks, can be soluble in water. The covalent networks, better known as cross-linked hydrogels, are water-insoluble. Crosslinked hydrogels can be prepared from uncrosslinked hydrogels via an intra- or intermolecular chemical reaction of mutually reactive functional groups. If necessary cross-linking can be accomplished via a crosslinking agent as described hereinabove.

Therefore, an important aspect of the present invention relates to the conjugation of the hyaluronic acid derivatives, either cross-linked or water-soluble, with a pharmacologically or biologically active agent as well as a detectable label.

The pharmacologically or biologically active agent may be selected from an antibiotic, an antiinfective, an antimicrobial, an antiviral, a cytostatic, an antitumoral, an antiinflammatory, a wound healing agent, an anaesthetic, a cholinergic agonist, a cholinergic antagonist, an adrenergic agonist, an adrenergic antagonist, an antithrombotic, an antocoagulant, a haemostatic, a fibrinolytic, a thrombolytic agent, a growth factor (e.g. fibroblast growth factor), a cytokine, an antibody, a protein (e.g. fibrinogen), a protein fragment, a polypeptide, a peptide, a polynucleotide and a polymer.

The present invention further relates to a method for the preparation of a hyaluronic acid derivative of the invention in uncross-linked, water-soluble form, comprising reacting hyaluronic acid, activated by a carbodiimide, with hydrazine or a substituted hydrazine of the formula HNR1-HNR2, at a pH range of 3.5-7.5, preferably at 5.5-6.2, more preferably at 5.7-5.9. The reaction may be performed in one step by reaction of a mixture of hyaluronic acid, a carbodiimiode and a hydrazine or substituted hydrazine.

The hyaluronic add used for the preparation of the derivatives of the invention has an average molecular weight (M.W.) of from about 800 to about 4,000,000 Da.

The carbodiimide used in the invention are well known compounds as represented by the following formula:

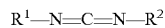

Carbodiimides having this formula are preferred where $R^1$ and/or $R^2$ represent more specifically alkyl, cycloalkyl, aryl, or substituted forms thereof. Most preferred are carbodiimides that are completely water-soluble or those that are soluble in mixtures of dipolar aprotic solvents and water. Representatives of the preferred carbodiimides are 1-ethyl-3-[3-dimethylaminopropyl]carbodiimide (EDC), cyclohexyl-β-(N-methylmorpholino)ethyl carbodiimide p-toluenesulfonate (CMC), N,N'-dicyclohexylcarbodiimide (DCC), N,N'-diisopropylcarbodiimide (DIC) and the like.

The molar ratio of hydrazine or substituted hydrazine to the HA carboxy groups may be between 1:1 to 80:1, preferably between 10:1 to 60:1, more preferably 40:1. The molar ratio of the carbodiimide (e.g. EDC) to the HA carboxy groups may be between 0.1:1 to 10:1, more preferably between 4:1 to 8:1. In general, increasing the molar ratio of carbodiimide to the HA carboxylic groups leads to a higher degree of hydrazido group formation.

The reaction may be performed in water or in an aqueous buffer, preferably aqueous Bis-Tris buffer. The concentration of the buffer may range between 50 mM to 500 mM preferably between 200 mM to 300 mM. The reaction may also be performed in a mixture of aqueous buffer and a water-soluble organic solvent such as hydrocarbyl alcohols, diols, glycerols or dipolar aprotic solvents. Preferably the water-miscible organic solvent is a dipolar aprotic solvent e.g. dimethyl sulfoxide, N,N-dimethylformamide, 1-methyl-2-pyrrolidone, 1,1,3,3-tetramethylurea, hexamethylphosphoramide, and acetonitrile.

The degree of hydrazido group formation can be measured using colorimetric techniques such as but not limited to the TNBS (2,4,6-trinitrobenzenesulfonic acid) procedure as described by Qi et al. (Analytical Biochem. 175:139-144, 1988). In this procedure, the reagent TNBS reacts covalently with a hydrazido group to form a highly chromogenic derivative, the color of which can be quantified spectrophotometrically. With the water insoluble cross-linked hydrazido functionalized HA only a qualitative estimation of the hydrazido groupd can be obtained, since the reaction between TNBS and the water insoluble derivatives produces chromogenic particles which partly precipitate from the assay's solution.

In another aspect, the invention provides a pharmaceutical composition containing a hyaluronic acid derivative of the invention, optionally in association with another pharmacological agent, and a pharmaceutically acceptable carrier.

The pharmaceutically acceptable carriers may be any of those conventionally used and are limited only by chemicalphysical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

In a further aspect, the invention provides a cosmetic composition containing a hyaluronic acid derivative of the invention, optionally in association with another cosmetic agent, and a cosmetically acceptable carrier.

Examples of the cosmetic agents that may be used according to the present invention include, but are limited to, xanthines, retinoids, α-hydroxy acids, β-hydroxy acids, hydroquinone, ascorbic acid, kojic acid, corticosteroids, mucopolysaccharides, collagen, isoflavonoids, cinnamic acid, benzoyl peroxide, tropolone, catechol, mercaptoamine, niacinamide, tocopherol, ferulic acid, azelaic acid, botulinum, urea, a derivative or salt thereof.

Examples of suitable cosmetic carriers include, but are not limited to, squalene, olive oil, corn oil, canola oil, peanut oil, safflower oil, flax oil, sunflower oil, mineral oil, castor, cetyl alcohol, stearyl alcohol, and stearic acid, as well as water-based carriers as glycerin, water, alcohol, propylene glycol and the like.

In another aspect, the invention provides a vehicle for slow release of therapeutics comprising hydrazido functionalized HA, said therapeutics being present in the bulk form of said functionalized HA.

In yet another aspect the cross-linked hydrazido functionalized HA of the invention may serve as an integral scaffolding material for tissue engineering as well as for wound or fracture healing either by itself, or as a substrate for cell delivery, e.g. the delivery of chondrocytes for repairing cartilage damage.

The invention will now be illustrated by the following non-limiting Examples.

The following abbreviations are used in the Examples:
EDC 1-ethyl-3-[3-dimethylaminopropyl]carbodiimide
HOBt 1-hydroxybenzotriazole
NHS N-hydroxysuccinimide
TNBS 2,4,6-trinitrobenzenesulfonic acid
DTSSP 3,3'-dithiobis [sulfosuccinimidylpropionate]
EDTA ethylenediaminetetraacetic acid
DTT Dithiothreitol
FITC fluorescein isothiocyanate
PEGDA poly(ethylene glycol)-butyrdialdehyde (M.W. 3400 Da)
DMS dimethyl suberimidate·2 HCl
PBS phosphate buffered saline
Bis-Tris 2,2-bis (hydroxymethyl)-2,2',2''-nitrilothiethanol
BSA bovine serum albumin
bFGF recombinant human basic fibroblast growth factor
ELISA enzyme-linked immunosorbent assay
The reagents EDC, HOBt, NHS, TNBS, DTT, EDTA, FITC, BSA and hydrazine hydrate, the buffers PBS and Bis-Tris, the solvents DMSO and 1-methyl-2-pyrrolidone, and the enzyme sheep testicular hyaluronidase were all obtained from Sigma (Weizmann Science Park, Israel).

The homobifunctional cross-linkers DTSSP, DMS and glutaraldehyde were obtained from Pierce. (Rockford, USA).

The homobifunctional cross-linked PEGDA was obtained from Nektar (San Carlos, USA).

bFGF was obtained from ProSpec TechnoGene (Weizmann Science Park, Israel).

Hyaluronic acid (M.W. 3,000,000 Da) was obtained as the commercially available sodium salt (sodium hyaluronate) and used throughout the experiments, unless otherwise indicated.

EXAMPLES

Example 1

Modification of HA with Hydrazine at pH 4.75 in Aqueous Solution

Hydrazine hydrate (44 mmol) was added to a solution of sodium hyaluronate (440 mg, 1.1 mmol carboxylic groups) in water (100 ml). The pH was adjusted to 4.75 by addition of 1N HCl. The solution was stirred for 10 min after which EDC (840 mg, 4.4 mmol) was added. The reaction mixture was stirred for additional 3 hours while maintaining the pH at 4.75 (0.1N, HCl). The reaction was stopped by raising the pH to 7.0 (0.1N NaOH).

Dialysis tubing with MW cutoff of 3500 daltons was soaked in water at room temperature for 3 hours and then rinsed with water. The reaction mixture was transferred into this tubing and exhaustively dialyzed with water.

The clear transparent mixture was filtered through a 0.45 µm membrane. A jelly-like water insoluble cross-linked product was isolated. The product was dried under vacuum to yield 420 mg of white fibers containing free hydrazido groups as confirmed qualitatively by the TNBS method.

Example 2

Modification of HA with Hydrazine at pH 4.75 in a Buffered Solution

A. Hydrazine hydrate (44 mmol) was added to solution of sodium hyaluronate (440 mg, 1.1 mmol carboxylic groups) in 100 ml buffer Bis-Tris (400 mM, pH 4.75). After adjusting the pH of this mixture to 4.75 (1N HCl), EDC (840 mg, 4.4 mmol) was added and the reaction mixture was stirred overnight. The pH was subsequently adjusted to 7.0 (0.1N NaOH).

A jelly-like water insoluble cross-linked-product was purified and isolated as described in example 1. The product contained free hydrazido groups as confirmed by the TNBS Method.

B. Performing the same procedure with half the amount of EDC (420 mg, 2.2 mmol) also resulted in a water insoluble cross-linked product containing free hydrazido groups.

Example 3

Preparation of Water-Soluble Hydrazido HA at pH 4.75

HA derivatized with N-acylurea groups (HA-EDC) was prepared from sodium hyaluronate and EDC according to established procedures (Bystricky et al., Chem. Pap. 1:49-52, 2001; Soltes et al., Biomed. Chromatogr. 17:376-384, 2003). The product contains about 40% blocked carboxylic functions.

HA-EDC (440 mg, 0.66 mmol carboxylic groups) was derivatized exactly as described in example 2B using the same amounts of hydrazine hydrate (44 mmol) and EDC (420 mg, 2.2 mmol).

The reaction mixture was dialyzed as described in example 1 against water (2 liters, 6 exchanges) for 72 hours. The dialyzed solution was filtered through 0.45 μm membrane, NaCl was added to the filtrate to produce a 5% w/v solution and the modified HA was precipitated by addition of three volume equivalents of ethanol. The product was dried under vacuum to yield 390 mg of white fibers. It contained 15% hydrazido groups as confirmed by the TNBS method.

Example 4

Modification of HA with Hydrazine at pH 5.5

Hydrazine hydrate (44 mmol) was added to a solution of sodium hyaluronate (440 mg, 1.1 mmol carboxylic groups) in 100 ml buffer Bis-Tris (400 mM, pH 5.5). After adjusting the pH of this mixture to 5.5 (1N HCl), EDC (840 mg, 4.4 mmol) was added and the reaction mixture was stirred overnight. The pH was subsequently adjusted to 7.0 (0.1N NaOH).

A jelly-like, water insoluble cross-linked product was purified and isolated as described in example 1. The product contained free hydrazido groups as confirmed by the TNBS method.

Example 5

Modification of HA with Hydrazine at pH 7.5

This modification was attempted following established procedures for the derivatization of HA with amines and hydrazides (Bulpitt and Aeschlimann, 1999; U.S. Pat. No. 6,630,457).

Hydrazine hydrate (44 mmols) was added to a solution of sodium hyaluronate (440 mg, 1.1 mmol carboxylic groups) in water (100 ml). The pH of the reaction mixture was adjusted to 7.5 (0.1N HCl). A mixture of EDC (840 mg, 4.4 mmol) and NHS (506 mg, 4.4 mmol) in $H_2O$ (2 ml) was added and the pH was adjusted to 7.5. The reaction was allowed to proceed overnight. The reaction mixture was dialyzed against water and the soluble product was isolated as described in example 3.

The product was proved to be unchanged HA with zero substitution of hydrazido groups as confirmed by the TNBS method.

Example 6

Modification of HA with Hydrazine at pH 6.8

This modification was also performed according to Bulpitt and Aeschlimann (1999) as described in the previous example.

Hydrazine hydrate (44 mmol) was added to a solution of sodium hyaluronate (440 mg, 1.1 mmol carboxylic groups) in water (100 ml). The pH of the reaction mixture was adjusted to 6.8 (0.1N HCl). A mixture of EDC (840 mg, 4.4 mmol) and HOBT (594 mg, 4.4 mmol) in DMSO/$H_2O$ (1:1, 2 ml) was then added and the pH was readjusted to 6.8. The reaction was allowed to proceed overnight. The reaction mixture was dialyzed against water and the soluble product was isolated as described in example 3.

The product was dried under vacuum to yield 400 mg of white fibers. It contained 3% hydrazido groups as confirmed by the TNBS method.

Example 7

Modification of HA with Hydrazine at pH 6.2

Hydrazine hydrate (44 mmol) was added to a solution of sodium hyaluronate (440 mg, 1.1 mmol carboxylic groups) in 100 ml buffer Bis-Tris (400 mM, pH 6.2). After readjusting the pH of this mixture to 6.2 (1N HCl), EDC (840 mg, 4.4 mmol) was added and the reaction mixture was stirred overnight. The pH was subsequently adjusted to 7.0 (0.1N NaOH).

The water soluble product was purified and isolated as described in example 3. The product was dried under vacuum to yield 400 mg of white fibers. It contained 3% hydrazido groups as confirmed by the TNBS method.

Example 8

Preparation of Water Soluble Hydrazido HA at pH 5.8

Hydrazine hydrate (44 mmol) was added to a solution of sodium hyaluronate (440 mg, 1.1 mmol carboxylic groups) in 100 ml buffer Bis-Tris (400 mM, pH 5.8). After readjusting the pH of this mixture to 5.8 (1N HCl), EDC (840 mg, 4.4 mmol) was added and the reaction mixture was stirred overnight. The pH was subsequently adjusted to 7.0 (0.1N NaOH).

The water soluble product was purified and isolated as described in example 3. The product was dried under vacuum to yield 400 mg of white fibers containing 12% hydrazido groups as confirmed by the TNBS method.

Increasing the amount of EDC to 8.8 mmol resulted in a product containing 20% hydrazido groups.

Derivatization of HA having molecular weights other than 3,000,000 Da, under identical conditions, also resulted in water-soluble HA products having ~12% hydrazido groups. HA with the following molecular weights were used:
a. M.W. 700,000 Da.
b. M.W. 250,000 Da obtained by acidic hydrolysis of HA (M.W. 3,000,000 Da) according to Shu et L., Biomacromolecules 3:1304-1311, 2002.

Example 9

Preparation of Water Soluble Hydrazido HA in a Mixture of Buffer and a Dipolar Aprotic Solvent Hydrazine hydrate (44 mmol) was added to a solution of sodium hyaluronate (440 mg, 1.1 mmol carboxylic groups) in 100 ml buffer Bis-Tris (400 mM, pH 5.8). After readjusting the pH of this mixture to 5.8 (1N HCl), DMSO (50 ml) was added followed by EDC (840 mg, 4.4 mmol). The reaction mixture was stirred overnight. The pH was subsequently adjusted to 7.0 (0.1N NaOH).

The water soluble product was purified and isolated as described in example 3. The product was dried under vacuum to yield 400 mg of white fibers containing 20% hydrazido groups as confirmed by the TNBS method.

An additional experiment was performed under identical conditions except for DMSO being replaced by 1-methyl-2-pyrrolidone. A water soluble hydrazido HA was obtained containing 19% hydrazido groups.

Example 10

Cross-Linking of Hydrazido-HA Using Homobifunctional Cross-Linkers

The presence of reactive hydrazido moieties on the HA backbone enable the introduction of a variety of covalent cross-links between individual HA strands using commercially available amine-specific homobifunctional cross-linkers such as: DTSSP, DMS, glutaraldehyde or PEGDA.

General procedure for cross-linking of hydrazido-functionalized HA with homobifunctional, cross-linkers:

Hydroazido functionalized HA containing 12% hydrazido groups (prepared as described in example 8) was dissolved in PBS buffer (pH 7.4) at concentrations varying from 0.2% to 1.5%.

Homobifunctional cross-linkers were added to the clear and colorless solutions and the mixtures were agitated for several seconds. The equivalency ratios of hydrazido-HA: cross-linkers were typically in the range of 1:05 to 1:10.

The details of some individual reactions are described below:
  a. Cross-linking with glutaraldehyde. Hydrazido-HA (16 mg) was dissolved in PBS (2 ml, pH 7.4). Glutaraldehyde diluted with PBS (200 µl) was then added. The molar ratio of hydrazido groups:glutaraldehyde was 1:0.5. The mixture was agitated for several seconds. A clear and transparent hydrogel was formed after one minute.
  b. Cross-linking with PEGDA. Hydrazido-HA (16 mg) was dissolved in PBS (2 ml, pH 7.4). PEGDA (6.8 mg) diluted in PBS (80 µl) was then added. The molar ratio of hydrazido groups:PEGDA was 1:0.5. The mixture was agitated for several seconds. A clear and transparent hydrogel was formed after several minutes.
  c. Cross-linking with DTSSP. Hydrazido-HA (16 mg) was dissolved in PBS (2 ml, pH 7.4). DTSSP (5 mg) was then added in solid form. The molar ratio of hydrazido groups:DTSSP was 1:1.6. The mixture was agitated for 30 seconds. A clear and transparent hydrogel was formed after 30 minutes.
  d. Cross-linking with DMS. Hydrazido-HA (20 mg) was dissolved in PBS (2 ml, pH 7.4). A solution of DMS (13 mg) in $H_2O$ (100 µl) was then added. The molar ratio of hydrazido groups:DMS was 1:10. The mixture was agitated for 30 seconds. A clear and transparent hydrogel was formed after 45 minutes.

Example 11

Comparative Experiment with Native HA

A control experiment was performed in parallel to the cross-linking experiments described above. Native (unmodified) HA was dissolved at a concentration of 10 mg/ml in PBS buffer (pH 7.4) DMS, DTSSP, Glutaraldehyde or PEGDA added to the viscous mixture and allowed to stir at room temperature. No gelatin of the solution was observed over time and the mixture components remained completely water soluble indicating that in the absence of hydrazido-functionalized HA no covalent cross-linking had taken place.

Example 12

Cross-Linking of Hydrazido-HA Using Polyaldehydes

A. Cross-linking with oxidized AH. To a solution of sodium hyaluronate (15 mg, 37.5 µmols) in $H_2O$ (3 ml), sodium periodate (8 mg, 37.5 µmols) was added and the reaction was allowed to proceed for two hours at room temperature. DTT (12 mg) was then added in order to destroy unreacted periodate. After 1.5 minutes, the reaction mixture was transferred into a dialysis tubing (MW cutoff 3500 daltons) and exhaustively dialyzed against PBS (pH 7.4). A solution of hydrazido-HA (15 mg, M.W. $2.5 \times 10^5$, 15% hydrazido groups) in PBS (1 ml, pH 7.4) was added to the above prepared solution of oxidized HA. The mixture was shortly agitated. A clear and transparent hydrogel was formed overnight.

B. Cross-linking with oxidized gelatin. Aldehyde functions were generated in gelatin by oxidizing its hydroxylysine residues according to the following procedure: sodium, periodate (7.5 mg) was added to a solution of gelatin (25 mg, Merck Cat. No. 104080) in acetate buffer (500 µl, 50 mM, pH 4.5). The reaction was allowed to proceed for 3 hours. DTT (38 mg) was then added in order to destroy unreacted periodate. After 60 minutes at room temperature, the solution was mixed with a solution of hydrazido-HA (5 mg, M.W. $3 \times 10^6$, 20% hydrazido groups) in acetate buffer (500 µl, 50 mM, pH 4.5). A clear and transparent hydrogel was formed after several minutes. An additional experiment was performed under identical conditions except for the acetate buffer being replaced by PBS (pH 7.4), however, at this slightly basic pH the hydrogel was formed only after 12 hours.

Example 13

Zero-Length Cross-Linking of Hydrazido HA with EDC

Hydrazido functionalized HA containing 20% hydrazido groups (prepared as described in example 9) was dissolved in Bis-Tris buffer (100 mM, pH 4.75) at various concentrations ranging from 0.2% to 1.5%.

Solid EDC was added at an equivalency ratio of EDC: carboxylic groups in the range of 0.5:1 to 4:1. The mixtures were agitated for several seconds. The gellation time depended on the concentration of EDC. The details of two individual reactions are described below:
  a. Hydrazido-HA (16 mg) was dissolved in 2 ml buffer Bis-Tris (100 mM, pH 4.75). EDC (4 mg) was added and the mixture was vigorously agitated for a few seconds. The molar ratio of EDC to carboxylic groups was 0.5:1. A clear and transparent hydrogel was formed after 3 hours.
  b. Hydrazido-HA (16 mg) was dissolved in 2 ml buffer Bis-Tris (100 mM, pH 4.75). EDC (32 mg) was added and the mixture was vigorously agitated for a few seconds. The molar ratio of EDC to carboxylic groups was 4:1. A clear and transparent hydrogel was formed within 1 minute.

When native (unmodified) HA was reacted with EDC using the exact conditions described above no hydrogels were formed.

Example 14

Digestion of Cross-Linked HA Hydrogels with Hyaluronidase

The two hydrogels described in the previous example (13a and b) were purified by repeated washings with PBS (pH 7.4) for 48 hours. Sheep testicular hyaluronidase (200 u/ml in PBS, 500 μl) was added to each hydrogel and incubated at 37° C. The hydrogel prepared using 4 mg EDC (example 12a) was completely dissolved within 4 hours. The second hydrogel (prepared using 32 mg EDC, example 12-b) was completely dissolved within 26 hours.

Example 15

Preparation of FITC-Labeled Hyaluronic Acid

FITC (0.5 mg, 1.25 μmols) in carbonate buffer (500 μl, 0.1M, pH 9) was added to a solution of hydrazido-HA (20 mg, M.W. $2.5 \times 10^5$, 10% hydrazido groups) in the same buffer (2 ml). The reaction was allowed to proceed at room temperature in the dark. After 1 hour, the reaction mixture was transferred into a dialysis tubing (M.W. cutoff 3500 daltons) and exhaustively dialyzed, in the dark, against PBS (pH 7.4) until the product was completely free of unreacted FITC and its low molecular weight side-products. The dialyzate was lyophilized to yield the product as a yellow solid. The degree of FITC-derivatized hydrazido groups was determined following the procedure described by Akira et al. (Carbohydrate Res. 105:69-85, 1982) and was found to be around 10%. The degree of the derivatization of the hydrazido groups in the above described reaction is controlled by the ratio FITC: hydrazido groups. For example, increasing the amount of FITC to 2 mg (5 μmols) lead to a derivatization degree of around 40% whereas using 4 mg (10 μmols) of FITC lead to a derivatization degree of around 60%.

Example 16

Incorporation of bFGF in a Cross-Linked Hydrazido-HA Hydrogel and its Release from the Hydrogel Hydrazido-HA (20 mg, M.W. $2.5 \times 10^5$, 10% hydrazido groups) was dissolved in PBS (2 ml, pH 7.4). A solution of bFGF (850 μg) in PBS (257 μl, supplemented with 1 mM EDTA, pH 7.40) was then added, followed by a solution of homobifunctional cross-linker PEGDA (9 mg) in PBS (110 μl, pH 7.4). The clear mixture was agitated for several seconds. A transparent hydrogel was formed within 30 minutes. The bFGF was released by agitating the hydrogel at room temperature at 100 rpm with PBS (2 ml, supplemented with 1% BSA and 1 mM EDTA, pH 7.4). The release medium was replaced every 24 hours and the collected samples (2 ml each) were stored at −70° C. until measurement. The amount of the released bFGF in each of the collected samples was measured using a bFGF ELISA kit, supplied by R&D Systems (Minneapolis, Minn., USA, Catalog No. DY 233), according to the manufacturer instructions. It was found that after a cumulative release time of 240 hours, 77.6% (660 μg) of the incorporated bFGF was released.

The invention claimed is:

1. A cross linked hydrazido modified hyaluronic acid, of formula HA-CO—NH—NH—CO-HA formed by crosslinking a hyaluronic acid derivative of formula HA-CO—NH—NH₂ or a salt thereof, said derivative having a part of the carboxy groups of the D-glucuronic residues modified into hydrazido groups.

2. The cross linked hydrazido modified hyaluronic acid of claim 1, wherein said crosslinked hydrazido modified hyaluronic acid is formed by reaction of a part of the hydrazido groups of the D-glucuronic residues with a part of the carboxy groups of the D-glucuronic residues, said carboxy groups being activated by a carbodiimide.

3. A crosslinked hydrazido modified hyaluronic acid of formula HA-CO—NH—NH—Y—NH—NH—CO-HA formed by crosslinking a hyaluronic acid derivative of formula HA-CO—NH—NH₂, or a salt or derivative thereof, said derivative having a part of the carboxy groups of the D-glucuronic residues modified into hydrazido groups; wherein Y is an aliphatic, aromatic, arylaliphatic, cycloaliphatic or heterocyclic chain, and wherein said crosslinked hydrazido modified hyaluronic acid is formed by reaction of a part of the hydrazido groups of the D-glucuronic residues with another part of the hydrazido groups of the D-glucuronic residues via an amine-specific or amine-reactive linker selected from a bisaldehyde and a polyaldehyde.

4. The crosslinked hydrazido modified hyaluronic acid according to claim 3 wherein said bisaldehyde is a member of the group consisting of glutaraldehyde, poly(ethylene glycol)-propriondialdehyde and poly(ethylene glycol)-butyraldialehyde.

5. The crosslinked hydrazido modified hyaluronic acid according to claim 4 wherein said polyaldehyde is selected from the group consisting of oxidized collagen, oxidized gelatin and oxidized hyaluronic acid; and wherein said collagen is selected from any type of natural, denatured or derivatized collagen.

6. A crosslinked hydrazido modified hyaluronic acid according to claim 5 wherein said cross linked hydrazido modified hyaluronic acid further comprises uncrosslinked hydrazido groups available for further derivatization.

7. A crosslinked hydrazido modified hyaluronic acid according to claim 5 wherein said crosslinked hydrazido modified hyaluronic acid is conjugated with a pharmacologically or biologically active agent selected from the group consisting of: an antibiotic, an antiinfective, an antimicrobial, an antiviral, a cytostatic, an anti-tumoral, an anti-inflammatory, a wound healing agent, an anaesthetic, a cholinergic agonist, a cholinergic antagonist, an adrenergic agonist, an adrenergic antagonist, an antithrombotic, an anticoagulant, a haemostatic, a fibrinolytic, a thrombolytic agent, a growth factor, a cytokine, an antibody, a protein, a protein fragment, a polypeptide, a peptide, a polynucleotide and a polymer.

8. The crosslinked hydrazido modified hyaluronic acid according to claim 7, wherein said crosslinked hydrazido modified hyaluronic acid has between 0.5% and 70% of the carboxy moieties of D-glucuronic groups modified into hydrazido groups and an average molecular weight of from about 800 to about 4,000,000 Da.

9. The crosslinked hydrazido modified hyaluronic acid according to claim 7, wherein said crosslinked hydrazido modified hyaluronic acid is in the form of a hydrogel.

10. A pharmaceutical composition comprising a cross linked hydrazido modified hyaluronic acid according to claim 7 further comprising a pharmaceutically acceptable carrier; and optionally a pharmacologically active agent chemically conjugated or unconjugated; and wherein said pharmaceutical composition is capable of providing slow release or sustained release of said pharmaceutically active agent.

11. A cosmetic composition comprising a crosslinked hydrazido modified hyaluronic acid according to claim 7, further comprising a cosmetically acceptable carrier, and a cosmetic agent.

12. A composition comprising a crosslinked hydrazido modified hyaluronic acid according to claim 1, further comprising a member selected from the group consisting of native or synthetic polymers, proteins, or polypeptides.

13. A method for preparation of the crosslinked hydrazido modified hyaluronic acid of claim 1 comprising activating said hyaluronic acid derivative with a carbodiimide at a pH range of between pH3.5 and pH 7.0.

14. A method for preparation of the crosslinked hydrazido modified hyaluronic acid of claim 1 comprising activating said hyaluronic acid derivative with a carbodiimide and reacting said hyaluronic acid derivative with hydrazine at between pH 3.5 and 7.0.

* * * * *